United States Patent [19]

Freter et al.

[11] 4,359,468
[45] Nov. 16, 1982

[54] ANTIALLERGIC N-[4-(INDOLYL)-PIPERIDINO-ALKYL]-BENZIMIDAZOLONES

[75] Inventors: Kurt Freter, Ridgefield; Victor Fuchs, New Fairfield; James T. Oliver, Middlebury, all of Conn.

[73] Assignee: Boehringer Ingelheim Ltd., Ridgefield, Conn.

[21] Appl. No.: 237,966

[22] Filed: Feb. 25, 1981

[51] Int. Cl.³ .................... A61K 31/445; C07D 401/14
[52] U.S. Cl. ................................ 424/267; 546/199; 546/201; 546/271; 546/273
[58] Field of Search ................. 546/199, 201; 424/267

[56] References Cited

U.S. PATENT DOCUMENTS

| 3,954,764 | 5/1976 | Gerecke et al. | 424/250 X |
| 3,980,658 | 9/1976 | Possanza et al. | 546/201 |
| 4,147,786 | 4/1979 | Huebner | 546/201 X |

FOREIGN PATENT DOCUMENTS 1404003  8/1975  United Kingdom ................ 546/199

Primary Examiner—Richard A. Schwartz

Attorney, Agent, or Firm—Hammond & Littell, Weissenberger & Muserlian

[57] ABSTRACT

Compounds of the formula

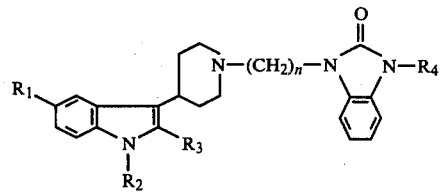

wherein
 $R_1$ is hydrogen, halogen or methoxy;
 $R_2$ is hydrogen or lower alkyl;
 $R_3$ is hydrogen or lower alkyl;
 $R_4$ is hydrogen, lower alkyl or alkenyl of 3 carbon atoms; and
 n is 2 to 6;

and non-toxic, pharmacologically acceptable acid addition salts thereof. The compounds as well as their salts are useful as antiallergics and hypotensives.

5 Claims, No Drawings

ANTIALLERGIC N-[4-(INDOLYL)-PIPERIDINO-ALKYL]-BENZIMIDAZOLONES

FIELD OF THE INVENTION

This invention relates to novel substituted N-[4-(indolyl)-piperidino-alkyl]-benzimidazolones and non-toxic acid addition salts thereof, to methods of preparing these compounds, to pharmaceutical composition containing them as active ingredients, and to methods of using them as antiallergics and hypotensives.

THE PRIOR ART

U.S. Pat. No. 3,950,527 discloses certain N-[ω-(4'-(3'-indolyl)-piperidino)-alkyl]-benzamides having sedative and tranquilizing properties.

U.S. Pat. No. 4,100,291 discloses certain α-(1,4-benzodioxinyl)-4-indolyl-1-piperidine-ethanols having antihypertensive properties.

THE INVENTION

More particularly, the present invention relates to a novel class of compounds represented by the formula

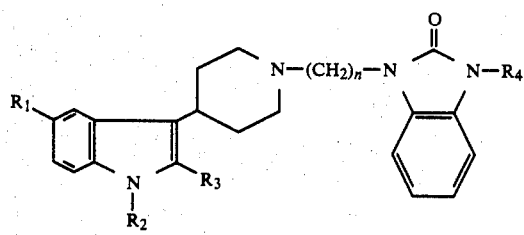

wherein
- $R_1$ is hydrogen, halogen or methoxy;
- $R_2$ is hydrogen or lower alkyl;
- $R_3$ is hydrogen or lower alkyl;
- $R_4$ is hydrogen, lower alkyl or alkenyl of 3 carbon atoms; and
- n is 2 to 6;

and non-toxic, pharmacologically acceptable acid addition salts thereof.

The term "halogen" is intended to include fluorine, chlorine and bromine.

The term "lower alkyl" is intended to designate alkyl of 1 to 3 carbon atoms, preferably methyl.

The compounds embraced by formula I may be prepared by various methods involving known chemical synthesis principles, among which the following are preferred.

Method A

By alkylating a 3-(1,2,5,6-tetrahydro-4-pyridyl)-indole of the formula

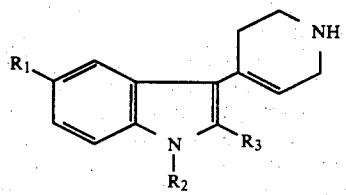

wherein $R_1$, $R_2$ and $R_3$ have the same meanings as in formula I, with an N-(ω-haloalkyl)-benzimidazolone of the formula

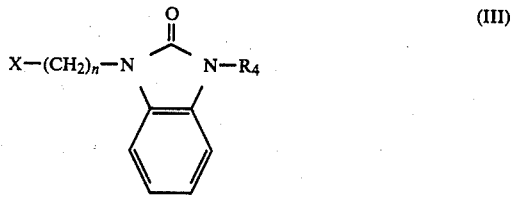

wherein
- $R_4$ and n have the same meanings as in formula I, and
- X is chlorine, bromine or iodine, and hydrogenating the resulting intermediate of the formula

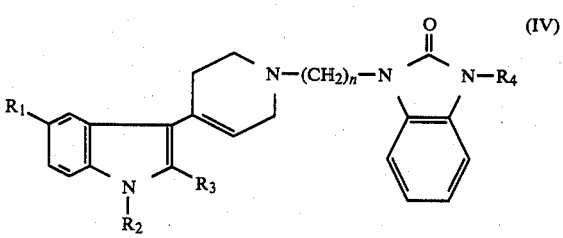

with hydrogen in the presence of a noble metal catalyst.

The alkylation reaction is performed in the presence of an inert polar or non-polar organic solvent, such as ethanol, dimethyl formamide, terahydrofuran or the like, and advantageously in the presence of an inorganic or organic acid-binding agent such as sodium hydroxide, sodium carbonate, sodium bicarbonate, triethylamine or the like at temperatures between 20° C. and the boiling point of the solvent.

The subsequent hydrogenation is carried out at a temperature of 20° C. at atmospheric or elevated pressure.

Examples of suitable noble metal catalysts are palladium and platinum.

Method B

By alkylating a 3-(4-piperidyl)-indole of the formula

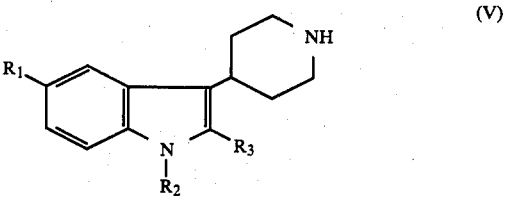

wherein $R_1$, $R_2$ and $R_3$ have the same meanings as in formula I, with an N-(ω-halo-alkyl)-benzimidazolone of the formula III.

The alkylation reaction is performed in the presence of an inert polar or non-polar organic solvent, such as ethanol, dimethyl formamide, tetrahydrofuran or the like, and advantageously in the presence of an inorganic or organic acid-binding agent such as sodium hydroxide, sodium carbonate, sodium bicarbonate, triethylamine or the like at temperatures between 20° C. and the boiling point of the solvent.

Method C

By alkylating 4-piperidone of the formula

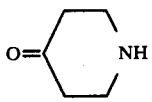  (VI)

with an N-(ω-halo-alkyl)-benzimidazolone of the formula III to form an intermediate of the formula

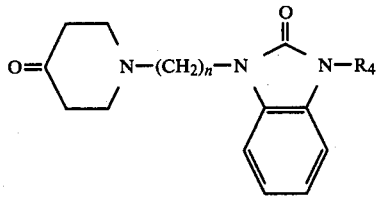  (VII)

wherein $R_4$ and n have the same meanings as in formula I, reacting said intermediate in acid solution with an indole of the formula

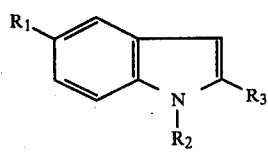  (VIII)

wherein $R_1$, $R_2$ and $R_3$ have the same meanings as in formula I, to form the corresponding intermediate of the formula IV, and hydrogenating the latter as in method A.

The reaction of intermediate VII with the indole of the formula VIII is carried out in aqueous acid solution at room temperature.

Method D

By alkylating a 3-(4-piperidyl)-indole of the formula V with an α,ω-dihalo-alkane of the formula

  (IX)

wherein n has the same meanings as in formula I, and each X is independently chlorine, bromine or iodine, to form the intermediate of the formula

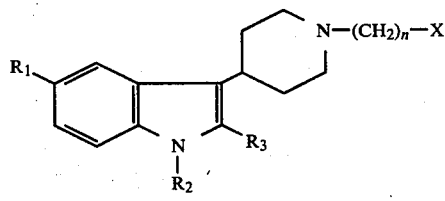  (X)

wherein $R_1$, $R_2$, $R_3$, n and X have the meanings previously defined, and alkylating said intermediate with a benzimidazolone of the formula

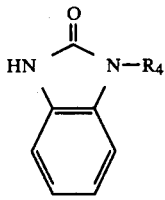  (XI)

wherein $R_4$ has the same meanings as in formula I.

The compounds embraced by formula I are basic and therefore form addition salts with inorganic or organic acids. Examples of non-toxic, pharmacologically acceptable acid addition salts are those formed with hydrohalic acid, especially hydrochloric or hydrobromic acid, nitric acid, sulfuric acid, o-phosphoric acid, tartaric acid, citric acid, maleic acid, fumaric acid, propionic acid, butyric acid, acetic acid, succinic acid, methanesulfonic acid, benzenesulfonic acid, p-toluenesulfonic acid, or the like.

The starting compounds for methods A through D are known compounds or may be prepared by known methods.

Compounds of the formula II and methods for their preparation are described by K. Freter in J. Org. Chem. 40, 2525 (1975).

Compounds of the formulas III and XI are described by F. Awouters et al. in "Drugs Affecting the Respiratory System," ACS Symposium Series 118, page 179 (1980).

Compounds of the formula V and methods for their preparation are described by D. Beck et al. in Helv. Chim. Acta 51, 260 (1968).

Compounds of the formulas VI and VIII are commercially available from Aldrich Chemical Co., Inc., Milwaukee, Wisc.

The following examples illustrate the present invention and will enable others skilled in the art to understand it more completely. It should be understood, however, that the invention is not limited solely to the particular examples given below.

EXAMPLE 1

N-{3-[4-(2-Methyl-3-indolyl)-piperidino]-propyl}-benzimidazolone and its hydrochloride by method A.

A mixture consisting of 1.06 gm of 2-methyl-3-(1,2,5,6-tetrahydropyridyl-4)-indole, 1.05 gm of N-(3-chloro-propyl)-benzimidazolone, 0.42 gm of sodium bicarbonate, 20 ml of dimethylformamide and 20 ml of tetrahydrofuran was heated at 100° C. for 18 hours while stirring. Thereafter, the reaction mixture was poured into a mixture of 200 gm of ice and 10 ml of concentrate ammonia, and the precipitate formed thereby was collected by filtration and recrystallized from ethanol, yielding 1.2 gm (62% of theory) of the intermediate of the formula IV ($R_1$=H, $R_2$=H, $R_3$=—$CH_3$, n=3, $R_4$=H) having a melting point of 215° C.

1.5 gm of the intermediate thus obtained were dissolved in 100 ml of acetic acid and shaken for 24 hours with 0.8 gm of palladium —5%-on-charcoal at 20° C. in an atmosphere of hydrogen at 5 atmospheres pressure. Thereafter, the catalyst was removed by filtration, and the filtrate was poured into a mixture of ice and ammonia, whereupon the desired free base product precipitated. The precipitate was collected by filtration, dried, dissolved in ethanol and converted into its hydrochloride by addition of etheric hydrogen chloride. 1.05 gm (70% of theory) of the compound of the formula

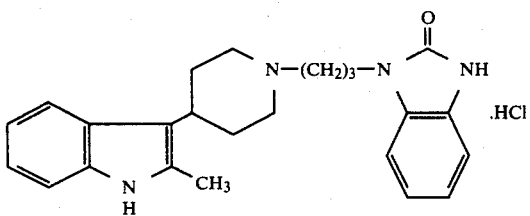

with a melting point of 264°–269° C. were obtained.

EXAMPLE 2

N-{4-[4-(3-Indolyl)-piperidino]-butyl}-benzimidazolone by method B

A mixture consisting of 3.0 gm of 4-(3-indolyl)-piperidine, 4.0 gm of 1-(4-chloro-butyl)-3-isopropenylbenzimidazolone, 1.3 gm of sodium bicarbonate, 30 ml of dimethyl-formamide and 30 ml of tetrahydrofuran was refluxed for 16 hours. Thereafter, the reaction mixture was poured into a mixture of ice and ammonia, the aqueous mixture was extracted with ethyl acetate, and the extract solution was washed with water, dried and evaporated to dryness in vacuo. The residue was dissolved in ether, etheric hydrogen chloride was added to the solution, and the precipitate formed thereby was collected by filtration, dried and dissolved in 100 ml of ethanol. The resulting solution was cooled, 16 ml of concentrated sulfuric acid were carefully added while stirring, and the mixture was allowed to stand at 20° C. for two hours, whereupon it was poured into a mixture of ice and ammonia. The precipitate formed thereby was collected by filtration and recrystallized from ethanol, yielding 3.2 gm (55% of theory) of the compound of the formula

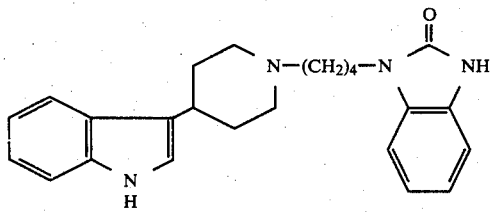

having a melting point of 196° C.

EXAMPLE 3

N-{3-[4-(1-Methyl-3-indolyl)-piperidino]-propyl}-benzimidazolone by method C

A mixture of 6.3 gm of N-(3-chloropropyl)-benzimidazolone, 4.6 gm of 4-piperidine hydrochloride monohydrate, 5.0 gm of sodium bicarbonate, 50 ml of tetrahydrofuran, and 50 ml of dimethylformamide, was heated to reflux, for 36 hours. The product was worked up as usual, yielding 3.2 gm (39% of theory) of N-[3-(4-oxo-piperidino)-propyl]-benzimidazolone, m.p. 134°–136° C.

A mixture consisting of 2.7 gm of N-[3-(4-oxopiperidino)-propyl]-benzimidazolone, 1.3 gm of 1-methylindole, 40 ml of acetic acid and 10 ml of 2 N phosphoric acid was allowed to stand at 20° C. for 6 days. Thereafter, the reaction mixture was poured into a mixture of ice and ammonia, the aqueous mixture was extracted with ethyl acetate, and the extract solution was dried and evaporated in vacuo to dryness. The residue was purified by chromatography on silica, using methylene chloride/methanol/ammonia=90/9/1 as the eluant. The main fraction was hydrogenated without characterization as described in Example 1, and the end product was crystallized from ethanol, yielding 2.4 gm (62% of theory) of the compound of the formula

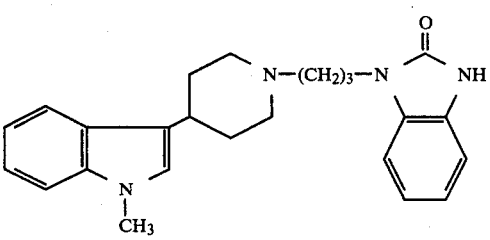

having a melting point of 180° C.

EXAMPLE 4

Using a procedure analogous to that described in Example 1, N-{3-[4-(3-indolyl)-piperidino]-propyl}-benzimidazolone and its hydrochloride, m.p. 204° C., were prepared from 3-(1,2,3,4-tetrahydropyridyl-4)-indole and N-(3-chloro-propyl)-benzimidazolone.

EXAMPLE 5

Using a procedure analogous to that described in Example 2, N-{3-[4-(5-methoxy-3-indolyl)-piperidino]-propyl}-benzimidazolone and its hydrochloride, m.p. 178° C., were prepared from 4-(5-methoxy-3-indolyl)-piperidine and N-(3-chloro-propyl)-benzimidazolone.

EXAMPLE 6

Using a procedure analogous to that described in Example 2, N-{3-[4-(3-indolyl)-piperidino]-propyl}-N'-isopropenyl-benzimidazolone, m.p. 68° C., was prepared from 4-(3-indolyl)-piperidine and N-(3-chloropropyl)-N'-isopropenyl-benzimidazolone.

EXAMPLE 7

Using a procedure analogous to that described in Example 2, N-{3-[4-(1-isopropyl-3-indolyl)-piperidino]-propyl}-benzimidazolone and its hydrochloride, m.p. 145° C., were prepared from 4-(1-isopropyl-3-indolyl)-piperidine and N-(3-chloro-propyl)-benzimidazolone.

EXAMPLE 8

Using a procedure analogous to that described in Example 2, N-{2-[4-(3-indolyl)-piperidino]-ethyl}-benzimidazolone, m.p. 116° C., was prepared from 4-(3-indolyl)-piperidine and N-(2-chloro-ethyl)-benzimidazolone.

EXAMPLE 9

Using a procedure analogous to that described in Example 2, N-{3-[4-(3-indolyl)-piperidino]-propyl}-N'-methyl-benzimidazolone and its hydrochloride, m.p. 140° C., were prepared from 4-(3-indolyl)-piperidine and N-(3-chloro-propyl)-N'-methyl-benzimidazolone.

EXAMPLE 10

Using a procedure analogous to that described in Example 3, N-{3-[4-(1-propyl-3-indolyl)-piperidino]-propyl}-benzimidazolone, m.p. 103° C., was prepared from N-[3-(4-oxopiperidino)-propyl]-benzimidazolone and 1-propyl-indole.

EXAMPLE 11

Using a procedure analogous to that described in Example 2, N-{3-[4-(2-methyl-5-chloro-3-indolyl)-piperidino]-propyl}-benzimidazolone, m.p. 124° C., was prepared from 4-(2-methyl-5-chloro-3-indolyl)-piperidine and N-(3-chloropropyl)-benzimidazolone.

EXAMPLE 12

Using a procedure analogous to that described in Example 2, N-{5-[4-(3-indolyl)-piperidino]-pentyl}-benzimidazolone, m.p. 137°-140° C., was prepared from 4-(3-indolyl)-piperidine and N-(5-bromo-pentyl)-benzimidazolone, m.p. 72°-75° C.

EXAMPLE 13

Using a procedure analogous to that described in Example 2, N-{6-[4-(3-indolyl)-piperidino]-hexyl}-benzimidazolone, m.p. 127°-130° C., was prepared from 4-(3-indolyl)-piperidine and N-(6-bromo-hexyl)-benzimidazolone, m.p. 103°-105° C.

EXAMPLE 14

N-{3-[4-(3-Indolyl)-piperidino]-propyl}-N'-isopropenylbenzimidazolone by method D A mixture of 2 gm of 4-(3-indolyl)-piperidine (V, $R_1$, $R_2$, $R_3$=H), and 20 ml of 1-bromo-3-chloro-propane was stirred at room temperature for 72 hours. The mixture was then extracted with 1 N hydrochloric acid. The extracts were made slightly basic with sodium carbonate and the product was extracted with ethyl acetate. The residue, 1-chloropropyl-4-(3-indolyl)-piperidine, after drying and evaporation was used without purification.

0.5 gm of the above intermediate were dissolved in 5 ml tetrahydrofuran and added to a cooled suspension of N-isopropenyl-benzimidazolone sodium salt prepared from 0.34 gm of N-isopropenyl-benzimidazolone and 0.05 gm of sodium hydride in 5 ml of dimethylformamide. The mixture was stirred for 16 hours at room temperature and then poured on ice-water-ammonia. The crystalline product was filtered off and dried. Yield: 0.65 gm (81% of theory), m.p. 68° C., identical with the product obtained by method B in Example 6.

The compounds of the present invention, that is, those embraced by formula I above and their non-toxic, pharmacologically acceptable acid addition salts, have useful pharmacodynamic properties. More particularly, they exhibit anti-allergic activity in warm-blooded animals such as rats, and are therefore useful for the treatment of allergic diseases such as allergic asthma, rhinitis, conjunctivitis, hay fever, urticaria, food allergies and the like.

Their pharmacological evaluation indicates that they act through two biological mechanisms: First, they stabilize the mast cells, thus preventing the release of mediators, the normal consequence of antigen-antibody reaction or other stimuli. Secondly, they possess antihistaminic properties, which is to say that they prevent the actions of histamine, the main mediator in human allergic disorders. The first property was demonstrated in the Mast Cell Stabilization Assay, the second one in Antihistamine Assays, and both together in the Passive Cutaneous Anaphylaxis Test as follows:

Rat Passive Cutaneous Anaphylaxis (PCA) Test

The test used was essentially that described by El-Azab, J. and Stewart, P. B., "Pharmacological Profile of a New Anti-Allergic Compound PRD-92-EA." Int. Archs. Allergy Appl. Immunol. 55: 350-361, 1977;

A dilution of anti-OA reaginic serum was used to give reproducible skin reactions with diameters between 10-15 mm in unsensitized rats. This anti-serum dilution was injected in a volume of 0.1 ml intradermally on each side of the shaved backs of male CD rats (150-160 gm) before antigen challenge. Test compounds which were evaluated by the intravenous (i.v.) route were dissolved in water, and mixed with 0.5 ml of a solution containing 5 mg ovalbumin and 2 percent Evans Blue and administered at a volume of 1 ml/kg. This mixture was injected 24 hours after the rats had been passively sensitized. For evaluation of oral activity, the test compound was suspended in a 1 percent acacia and administered in a volume of 1 ml/kg with an oral feeding needle. Twenty to thirty minutes after oral administration of the test substance, an antigenic challenge consisting of 0.015 mg of ovalbumin in 0.5 ml of 2% Evans Blue was administered. Fifteen minutes after antigenic challenge an intradermal injection of histamine, 3 μg/0.1 ml in saline was given to assess potential antihistaminic activity.

Thirty minutes after antigenic challenge, i.e. for either intravenous or oral administration, the rats were killed by $CO_2$ asphyxiation. A midline incision was made along the spine and the skin was reflected and the diameter of the blued areas were measured in millimeters. The mean area in square millimeters was determined for each spot and the mean circular area of that test group was calculated. The mean area in square millimeters of an untreated control group was considered as a 100 percent response, and the results of the test compound groups were expressed as a percent change from the control values. An $ED_{50}$ (i.e. defined as a 50 percent reduction in area) was determined using the method of Litchfield, J. T. Jr. and Wilcoxon, F. "A simplified Method of evaluating Dose-Effect Experiments," J. Pharmacol. Exp. Therap. 96: 99-113, 1949.

In Vivo Inhibition of Histamine-Induced Blueing in Rat Skin

Male CD rats (150-160 gm) were divided into two groups. The hair was removed from an area of the back with an electric clipper. An untreated control group received 10 ml/kg, p.o. of normal saline in 1 percent acacia. Experimental groups received test compound suspended in 1 percent acacia at a volume of 10 ml/kg, p.o. Two percent Evans Blue dye in normal saline in a volume of 0.5 ml was administered intravenously to all animals. Twenty minutes following administration of the test compound or vehicle, 3 μg of histamine diphosphate in 0.1 ml of normal saline was injected intradermally in two sites of the shaved area on the backs of the rats. Fifteen minutes following histamine injection, all rats were killed by $CO_2$ asphyxiation.

An incision was made along the spine and the skin cleanly separated. The dorsal skin was reflected and the diameters of the blue-spotted wheals were measured. The area in square millimeters was determined for each resulting blue spot and the mean area for the control and test groups were calculated. The mean area for the control group was considered as a 100 percent response. Test group results were expressed as a percentage change from control. An $ED_{50}$ (i.e., defined as a 50 percent reduction in blue-spotted area) was determined by linear regression analysis.

Inhibition of Peritoneal Mast Cell Degranulation (MCD) in Rats Passively Sensitized with OA Antiserum or Induced by Compound 48/80

This test was adapted from that described by Mota, I. and Osler, A. G. "Mast Cell Degranulation," *Methods in Medical Research* (ed. H. H. Eisen), Yearbook Medical Publication, Chicago, 1964.

Male CD rats (150-160 gm) were divided into 5 groups as follows:
Group I: Nonspecific MCD control (3 rats)
Group II: Positive MCD control (5 rats)
Groups III, IV, V: Positive MCD following test compound (5 rats each)

Group I was injected intraperitoneally with 3 ml of normal rat serum. Groups II through V were intraperitoneally administered 3 ml of an antiserum predetermined to produce a 60-80 percent greater degranulation than normal rat serum. Eighteen to 24 hours later, test compound was administered (i.e., i.v. immediately, i.p. 5 minutes, or p.o. 20 minutes) before i.p. antigen challenge with 0.5 mg/kg of 2×crystalline ovalbumin in a concentration of 0.005 percent saline. Fifteen minutes after challenge, the rats were killed by asphyxiation with $CO_2$.

In the case of experiments utilizing Compound 48/80 (N-methyl-homoanisylamine-formaldehyde-copolymer) to induce degranulation of the mast cells, Group I was injected intraperitoneally with 3 ml of Hank's solution at a pH of 7.2-7.4. The positive control group and groups receiving test compound were injected i.p. with 20 μg/kg of Compound 48/80 in 3 ml of Hank's solution at a pH of 7.2-7.4. The rats were killed by asphyxiation with $CO_2$ five minutes after the i.p. injection of Compound 48/80.

Microscopic slides of the mesentery were prepared and analyzed by a modification of the method by Fügner, A. "An Improved Method for the Study of Reaginmediated Mast Cell Degranulation in Rats," *Experientia*, 29: 708, 1973, to determine the degree of degranulation of mast cells in untreated and treated groups of rats.

The results were calculated and expressed as percent of inhibition of degranulation as follows:

Percent Inhibition =

$$100 - \left[ \frac{\text{Experimental} - \text{negative cont.}}{\text{Positive Cont.} - \text{Negative Cont.}} \right] \times 100$$

The following table shows the results obtained from these tests for a representative specie of the genus represented by formula I, namely the compound of Example 4, and oxatomide, a known compound of similar activity.

| Compound | PCA | $ED_{50}$'s mg/kg MCD | Antihist. |
|---|---|---|---|
| Oxatomide | 8.3 | neg. | 8.1 |
| Compound of Example 4 | 1.6 | 3.0-6.4 | 8.7 |

These results show that the compound of the present invention is superior in two respects, namely that it has demonstrable mast cell stabilizing in addition to antihistaminic properties and is some five times more potent.

For pharmaceutical purposes the compounds according to the present invention are administered to warm-blooded animals topically, perorally, parenterally or by the respiratory route as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, inhalation aerosols, ointments, emulsions, syrups, suppositories and the like. One effective dosage unit of the compounds according to the present invention is from 0.013 to 0.26 mgm/kg body weight.

The following examples illustrate a few pharmaceutical dosage unit compositions comprising a compound of the present invention as an active ingredient and represent the best modes contemplated of using the invention. The parts are parts by weight unless otherwise specified.

EXAMPLE 15

Tablets

The tablet composition is compounded from the following ingredients:

| | |
|---|---|
| N—{3-[4-(3-indolyl)-piperidino]-propyl}-benzimidazolone | 0.010 parts |
| Stearic acid | 0.010 parts |
| Dextrose | 1.890 parts |
| Total | 1.910 parts |

Preparation:
The ingredients are admixed in conventional manner, and the mixture is compressed into 1.91 gm-tablets, each of which is an oral dosage unit composition containing 10 mgm of the active ingredient.

EXAMPLE 16

Ointment
The ointment composition is compounded from the following ingredients:

| | |
|---|---|
| N—{3-[4-(3-indolyl)-piperidino]-propyl}-benzimidazolone | 2.000 parts |
| Fuming hydrochloric acid | 0.011 parts |
| Sodium pyrosulfite | 0.050 parts |
| Mixture (1:1) of cetyl alcohol and stearyl alcohol | 20.000 parts |
| White vaseline | 5.000 parts |
| Synthetic bergamot oil | 0.075 parts |
| Distilled water q.s. ad | 100.000 parts |

Preparation:
The ingredients are uniformly blended in conventional manner into an ointment, 100 gm of which contain 2.0 gm of the active ingredient.

EXAMPLE 17

Inhalation aerosol
The aerosol composition is compounded from the following ingredients:

| | |
|---|---|
| N—{3-[4-(3-indolyl)-piperidino]-propyl}-benzimidazolone | 1.00 parts |
| Soybean lecithin | 0.20 parts |
| Propellant gas mixture (Frigen | |

-continued

| 11, 12 and 14) | q.s. ad | 100.00 parts |

Preparation:

The ingredients are compounded in conventional manner, and the composition is filled into aerosol containers with a metering valve which releases 5 to 20 mgm of active ingredient per actuation of the valve.

EXAMPLE 18

Hypodermic solution

The solution is compounded from the following ingredients:

| N—{3-[4-(3-indolyl)-piperidino]-propyl}-benzimidazolone.HCl | | 5.0 parts |
| Sodium pyrosulfite | | 1.0 parts |
| Sodium salt of EDTA | | 0.5 parts |
| Sodium chloride | | 8.5 parts |
| Double-Distilled water | q.s. ad | 1000.0 parts |

Preparation:

The individual ingredients are dissolved in a sufficient amount of double distilled water, the solution is diluted to the indicated concentration with additional double-distilled water, the resulting solution is filtered until free from suspended particles, and the filtrate is filled under aseptic conditions into 1 ml-ampules which are subsequently sterilized and sealed. Each empule contains 5 mgm of the active ingredient.

Any one of the other compounds embraced by formula I or a non-toxic salt thereof may be substituted for the particular active ingredient in Examples 15 through 18. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

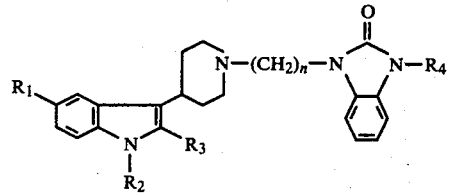

wherein $R_1$ is hydrogen, halogen or methoxy;

$R_2$ is hydrogen or lower alkyl;

$R_3$ is hydrogen or lower alkyl;

$R_4$ is hydrogen, lower alkyl or lower alkenyl;

n is 2 to 6;

or a non-toxic, pharmacologically acceptable acid addition salt thereof.

2. A compound of claim 1, which is N-{3-[4-(3-indolyl)-piperidino]-propyl}-benzimidazolone or a non-toxic, pharmacologically acceptable acid addition salt thereof.

3. A compound of claim 1, which is N-{4-[4-(3-indolyl)-piperidino]-butyl}-benzimidazolone or a non-toxic, pharmacologically acceptable acid addition salt thereof.

4. An antiallergic pharmaceutical composition consisting essentially of an inert pharmaceutical carrier and an effective antiallergic amount of a compound of claim 1.

5. The method of suppressing allergic reactions in a warm-blooded animal in need thereof, which comprises perorally, parenterally, topically or by inhalation administering to said animal an effective antiallergic amount of a compound of claim 1.

* * * * *